US011499935B2

United States Patent
Abdallah et al.

(10) Patent No.: US 11,499,935 B2
(45) Date of Patent: Nov. 15, 2022

(54) CLAY DETECTION AND QUANTIFICATION USING LOW FREQUENCY ELECTROMAGNETIC MEASUREMENTS

(71) Applicants: SCHLUMBERGER TECHNOLOGY CORPORATION, Sugar Land, TX (US); SAUDI ARABIAN OIL COMPANY, Dhahran (SA)

(72) Inventors: Wael Abdallah, Al-Khobar (SA); Ping Zhang, Al-Khobar (SA); Shouxiang Ma, Dhahran (SA); Chengbing Liu, Al-Khobar (SA)

(73) Assignees: SCHLUMBERGER TECHNOLOGY CORPORATION, Sugar Land, TX (US); SAUDI ARABIAN OIL COMPANY, Dhahran (SA)

( * ) Notice: Subject to any disclaimer, the term of this patent is extended or adjusted under 35 U.S.C. 154(b) by 0 days.

(21) Appl. No.: 16/663,673

(22) Filed: Oct. 25, 2019

(65) Prior Publication Data

US 2021/0123877 A1    Apr. 29, 2021

(51) Int. Cl.
*G01N 33/24*    (2006.01)
*G01N 27/22*    (2006.01)

(52) U.S. Cl.
CPC .......... *G01N 27/221* (2013.01); *G01N 33/24* (2013.01)

(58) Field of Classification Search
CPC ........ G01N 27/221; G01N 33/24; G01V 3/30; G01V 3/38; G09K 8/145
See application file for complete search history.

(56) References Cited

U.S. PATENT DOCUMENTS

| 4,584,874 A | 4/1986 | Ruhovets |
| 4,594,887 A | 6/1986 | Fertl et al. |
| 4,622,849 A | 11/1986 | Fertl |
| 4,712,424 A | 12/1987 | Herron |
| 4,722,720 A | 2/1988 | Herron |
| 4,756,189 A | 7/1988 | Fertl et al. |
| 4,903,527 A | 2/1990 | Herron |
| 4,953,399 A | 9/1990 | Fertl et al. |

(Continued)

FOREIGN PATENT DOCUMENTS

WO    2018067757 A1    4/2018

OTHER PUBLICATIONS

C-Y Hou et al. / journal of Colloid and interface Science 525 (2018) 62-75, herein mentioned Hou (Year: 2018).*

(Continued)

*Primary Examiner* — Jermele M Hollington
*Assistant Examiner* — Taqi R Nasir
(74) *Attorney, Agent, or Firm* — Trevor G. Grove (57) ABSTRACT

Methods and systems are provided for clay detection, clay typing, and clay volume quantification using electromagnetic measurements on a porous media sample at a low frequency less than 5000 Hz. The electromagnetic measurements are used to determine and store permittivity data that characterizes permittivity of the porous media sample at the low frequency less than 5000 Hz. The low frequency electromagnetic measurements can be performed in a laboratory, at a wellsite or other surface location. The low frequency electromagnetic measurements are nondestructive, and the results indicate that the methods and systems are highly sensitive to the existence of clays.

24 Claims, 7 Drawing Sheets

(56) References Cited

U.S. PATENT DOCUMENTS

| | | | |
|---|---|---|---|
| 6,646,437 | B1 | 11/2003 | Chitale et al. |
| 7,501,829 | B2 | 3/2009 | Davydychev et al. |
| 10,215,876 | B2 | 2/2019 | Zhang et al. |
| 11,237,292 | B2 | 2/2022 | Ma et al. |
| 2014/0107928 | A1* | 4/2014 | Roy .................. G01V 3/32 702/7 |
| 2014/0214324 | A1 | 7/2014 | Freedman et al. |
| 2016/0097876 | A1 | 4/2016 | Freed et al. |
| 2016/0187521 | A1* | 6/2016 | Homan ............... G01V 3/12 324/338 |
| 2017/0053046 | A1 | 2/2017 | Forsyth et al. |
| 2017/0315259 | A1 | 11/2017 | Quirein et al. |
| 2018/0164466 | A1* | 6/2018 | Zhang ................. G01V 3/28 |
| 2019/0086350 | A1 | 3/2019 | Cerepi et al. |
| 2019/0129056 | A1 | 5/2019 | Rasmus et al. |
| 2020/0025967 | A1 | 1/2020 | Zhang et al. |
| 2021/0124071 | A1 | 4/2021 | Zhang et al. |

OTHER PUBLICATIONS

Berligen, B. A. et al., "Estimation of Productivity of Lobo 6 Sand (Lower Wilcox, TX) by Identifying Diagenetic Clays Jsing Well Log Data," SPE 14278, 1985, SPE of AIME 60th annual Technical conference, Las Vegas, Nevada, U. S. A., 15 pages.

Charsky, A. et al., "Quantitative analysis of kerogen content and mineralogy in shale cuttings by Diffuse Reflectance nfrared Fourier Transform Spectroscopy", Paper SCA2012-27, Proceedings of the Society of Core Analysts 2012 International Symposium, Aberdeen, Scotland, 2012, 12 pages.

Fertl, W. H., "Gamma Ray Spectral Data Assists in Complex Formation Evaluation," transactions, 6th European SPWLA formation evaluation symposium, The Log Analyst, 1979, 20(5), pp. 3-37.

Freedman, R. et al., "New Method for Determining Mineralogy and Matrix Properties from Elemental Chemistry Measured by Gamma Ray Spectroscopy Logging Tools", SPE 170722, presented at the SPE Annual Technical Conference and Exhibition, Amsterdam, The Netherlands, 2014, 16 pages.

Hassan, M. et al., "Fundamentals of Differential Gamma Ray Log-Interpretation Techniques," Paper H, Transactions SPWLA, 1976, 18 pages.

Herron, S. et al., "Application and Quality Control of Core Data for the Development and Validation of Elemental Spectroscopy Log Interpretation" SPWLA-2014-LLL presented at the SPWLA 55th Annual Logging Symposium held in Abu Dhabi, UAE, 2014, pp. 1-23.

Johansen, J. B. et al., "Downhole neutron-induced spectroscopy element and mineral estimates compared to a ring-tested core reference," SWPAL-2019-0000 presented at the SPWLA 60th Annual Logging Symposium held in The Noodlands, Texas, U.S.A., 2019, 12 pages.

Kale, S. et al., "Rock Typing in Gas Shales," SPE 134539, presented at the SPE Annual Technical Conference and Exhibition held in Florence, Italy, 2010, 20 pages.

Kaufhold, S. et al., "Quantification of the mineralogical composition of clays using FIIR spectroscopy", Journal of Vibrational Spectroscopy, 2012, 59, p. 29-39.

Leroy, P. et al., "A triple-layer model of the surface electrochemical properties of clay minerals", Journal of Colloid and Interface Science, 2004, 270, pp. 371-380.

Macdonald, R. M. et al., "Comparison of Elemental and Mineral Abundances from Core and Three Modern Neutron nduced Elemental Spectroscopy Tools", SPWLA-2011-BBB, presented at the SPWLA 52nd Annual Logging Symposium, Colorado Springs, Colorado, U. S. A., 2011, 17 pages.

Macdonald, R. M. et al., "Comparison of Elemental and Mineral Abundances from Core and Three Modern Neutron nduced Elemental Spectroscopy Tools" Petrophysics, 2012, 53(4), pp. 272-284.

Matteson, A et al., "Quantitative mineral analysis by fourier transform infrared spectroscopy", 1993 SCA Conference Paper No. 9308, 16 pages.

Revil, A., "Spectral induced polarization of shaly sands: Influence of the electrical double layer", Water Resources Research, 2012, 48, W02517, 23 pages.

Sondergeld, C. H. et al., "Petrophysical Considerations in Evaluating and Producing Shale Gas Resources", SPE 131768, presented at the 2010 SPE Unconventional Gas Conference, Pittsburgh, Pennsylvania, U. S. A., 34 pages.

Hou, C.-Y. et al., "Low frequency complex dielectric (conductivity) response of dilute clay suspensions: Modeling and experiments", Journal of Colloid and Interface Science, 2018, 525, pp. 62-75.

International Search Report and Written Opinion of International Patent Application No. PCT/US2020/057106 dated Feb. 3, 2021, 11 pages.

Dargahi, et al., 2013, Clay Mineralogy of Shale Gas Reservoirs through Integrating Infrared Spectroscopy and X-Ray Diffraction, SPE 168908, Unconventional Resources Technology Conference held in Denver, Colorado, USA, Aug. 12-14, 2013 (10 pages).

Beckhoff, B. et al., (Eds.), 2007. Handbook of practical X-ray fluorescence analysis, Chapter 5 Quantitative Analysis, pp. 309-410.

Dudoignon and Pantet, 1998, Measurement and cartography of clay matrix orientations by image analysis and grey-evel diagram decomposition, Clay Minerals (1998), 33, 629-642.

Notice of Allowance issued in U.S. Appl. No. 16/663,636 dated Sep. 29, 2021, 14 pages.

International Preliminary Report on Patentability issued in PCT Application No. PCT/US2020/057106 dated May 5, 2022, 7 pages.

Office Action issued in U.S. Appl. No. 16/984,210 dated Jun. 8, 2022, 48 pages.

\* cited by examiner

CLAY DETECTION AND QUANTIFICATION USING LOW FREQUENCY ELECTROMAGNETIC MEASUREMENTS

FIELD

The present disclosure relates to methods and systems that can detect clay in a rock sample or other porous media sample and that can also determine data characterizing clay type and volume fraction of clay in the rock sample or other porous media sample.

BACKGROUND

Geological knowledge of formation rock is very critical for resources exploration, field development and production planning. To assess reservoir quality and the amount of hydrocarbons in-place, characterization of the mineralogy of the formation rock is needed in order to accurately calculate reservoir porosity and hydrocarbon saturation from logs. This is particularly true in the event that clay is present in the formation rock. Each hydrocarbon reservoir can contain different types of clays and different amounts of such clay types. Each clay type has its own different characteristics, which can be translated to what is called cation exchange capacity (CEC) in common petrophysical applications.

Clays are hydrous aluminum silicate minerals that are platy in structure and can form by the alteration of silicate minerals like feldspar and amphibole. Clays are commonly lumped or grouped into a number of clay types, including but not limited to smectite, kaolinite, chlorite, illite. Some clays have a tendency to swell when exposed to water, creating a potential drilling hazard when clay-bearing rock formations are exposed to water-base fluids during drilling, possibly reducing the permeability of a good reservoir rock. Some clays are used in drilling fluids to form an impermeable mudcake to isolate a formation from the invasion of drilling fluid. The structural differences amongst the clay types (smectite, kaolinite, chlorite, illite) can determine the surface area exposed to reservoir fluids or stimulating fluids. Clays can be found in pore spaces, as part of the matrix or as grain-cementing material. Authigenic clays, which grow in the pores from minerals in the connate water, can be pore-filling or pore-lining. These clays have considerable surface area exposed in the pore and can be reactive, while detrital clays that are part of the matrix are usually less reactive. Additionally, clays can be cementing, or grain-binding, materials that react with water or acid to disaggregate the formation if they are not protected by quartz overgrowths. The most common clays that create clay problems in hydrocarbon reservoirs are kaolinite, smectite, illite and chlorite.

Clays in formation rock can significantly impact estimation of hydrocarbon reserves and the methods and costs for producing the stored hydrocarbons from formation rock. In evaluating unconventional formation rock such as shale that contains clays, determining clay type and composition is a significant challenge considering the chemical complexity and heterogeneous nature of the unconventional formation rock.

In the downhole environment, gamma ray logs have been traditionally used to estimate formation shale/clay volume based on correlation related to inherent elements such as potassium, uranium and thorium.

Combining density, neutron and spectral natural gamma ray logs, one can determine clay density and neutron response to 100% clay at every depth and also determine clay volume independent of the clay types. Combining such knowledge allows the calculation of CEC and hydrogen index (HI), and from the CEC vs. HI crossplot, clay typing is possible.

In a laboratory setting, there are multiple techniques for elemental and mineralogical analysis for rock samples, most important are X-ray fluorescence (XRF), X-ray diffractometry (XRD), Fourier transform infrared spectroscopy (FTIR), and Diffuse reflectance infrared Fourier-transform spectroscopy (DRIFTS) in addition to qualitative thin section analysis under polarized transmitted light. In all cases, it is necessary to prepare the required samples to certain standards.

XRF is an electroscopic technique that employs a secondary or fluorescent emission generated by exciting a sample with a source of X-radiation. The energy absorbed by the atoms cause the production of secondary x-ray and fluorescence, emitted by the sample. The intensity of these secondary x-rays is proportional to the concentration of each element in the sample. XRF allows fast identification of elements heavier than Lithium ($Z=3$) in theory. But in practice, it is often difficult to quantify elements lighter than Sodium ($Z=11$). Currently, portable fluorescence devices allow real-time measurements, which translate to fast decisions making on the field. They offer the possibility to analyze samples without needing any previous preparation. Despite the advances in portable devices, the accuracy that can be expected from its results is still lower than the one that can be obtained by means of laboratory analytic techniques although it can be enhanced using reference samples. It is also noted that XRF measures elements, converting elements to minerals is an inversion process which may require calibrations and boundary conditions to ensure converging solutions.

In XRD, when an x-ray diffraction beam strikes the surface, the matter absorbs the radiation to a greater or lesser extent, depending on the different mechanisms of interaction that are registered, either fluorescent type or a disperse radiations. The dispersive one is constituted by the fraction of the incident energy that is emitted again without changing its wavelength. X-ray diffraction is a particular case of this type of radiation. The constant distances of each crystalline structure originate a characteristic distribution of maximums (peaks), which allows identifying the crystals qualitatively; the intensity of these peaks is proportional to the number of planes that diffract the incident beams, what happens just with certain angles of incidence. In such a case, a semi-quantitative concentration of a specific structure can be obtained by analyzing the area under the curve. Each peak is assigned to an intensity value and, with this information, the crystal or crystals to which the diffraction pattern investigated belongs are identified. Peaks of some minerals overlap and therefore depending on their concentration, minerals with little concentration can be completely mischaracterized with others. This can create large quantification error in sample mineral analysis which can be above 20% depending on the characterized mineral. In addition, for low angle diffraction lines (peaks) such as clays, the signal to noise ratio is usually poor, and due to the amount of disorders that can occur in clays structures, quantifying clays accurately is often difficult. It is also noted that XRD works only for crystalline, not for amorphous materials.

FTIR have been extensively used for mineral identification. Generally, sample preparation is extensive for FTIR. Specifically, potassium bromide (KBr) is mixed with specific mesh size sample powder and then pressed into a pellet and heated at 120° C. to remove water. Data is usually recorded in the range of 4000 to 400 cm$^{-1}$ using a spectral resolution of 4 cm$^{-1}$. FTIR can provide chemical and mineral information on complex samples such as shales without the need for separating clays. Although FTIR is a powerful technique for mineral characterization, it does have some limitations with respect to clay quantification.

Characterization of shales cannot be suitably performed using exclusively one technique. XRD was able to identify and quantify a number of different clay minerals, whereas FTIR was useful in confirming the presence of certain clays along with providing information about the poorly ordered materials and organic matter.

DRIFTS has recently been introduced as a commercial service for material mineralogy characterization. It is a fast and efficient technique for quantifying mineralogy from OBM-free core and cuttings samples. DRIFTS can be used in a laboratory or at a wellsite. It is not a downhole technique. It measures the vibrational absorbance due to chemical bonds and is capable of resolving illite, smectite, kaolinite, and chlorite. Samples are usually scanned as bulk powders without dilution in reflectance mode and spectra are collected over the mid-IR range from 375 to 4000 cm$^{-1}$ with 4 cm$^{-1}$ resolution.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

In accordance with the subject disclosure, methods and systems are provided for clay detection, clay typing, and clay volume quantification using electromagnetic measurements on a porous media sample at a low frequency less than 5000 hertz (Hz). The low frequency electromagnetic measurements are used to determine and store permittivity data that characterizes permittivity of the porous media sample at the low frequency less than 5000 Hz. The low frequency electromagnetic measurements can be performed in a laboratory, at a wellsite or other surface location. The low frequency electromagnetic measurements are nondestructive, and the results indicate that the methods and systems are highly sensitive to the existence of clays.

In embodiments, the methods and systems can employ a computational model that relates a parameter extracted from measurement of permittivity of porous media at a low frequency less than 5000 Hz to data that characterizes at least one clay type and corresponding clay volume fraction. Electromagnetic measurements can be conducted on a porous media sample at a low frequency less than 5000 Hz. The electromagnetic measurements can be used to determine and store permittivity data that characterizes permittivity of the porous media sample at the low frequency less than 5000 Hz. A parameter can be extracted from the permittivity data. The extracted parameter can be used as input to the computational model, wherein the computational model outputs data that characterizes at least one clay type and corresponding clay volume fraction for the porous media sample. The data that characterizes at least one clay type and corresponding clay volume fraction for the formation of interest as provided by the computational model can be stored or output for use.

In embodiments, the computational model can be derived by measuring permittivity of porous media of different known clay types and different clay volume fractions at the low frequency less than 5000 Hz (such as multiple low frequencies less than 5000 Hz) and correlating a parameter extracted from the resultant permittivity to data that characterizes at least one clay type and corresponding clay volume fraction.

In embodiments, the computational model can relate a parameter extracted from measurements of permittivity of porous media at multiple low frequencies less than 5000 Hz to data that characterizes at least one clay type and corresponding clay volume fraction. The permittivity data of the porous media sample as well as the parameter extracted from the permittivity data can be derived from the electromagnetic measurements of permittivity of the porous media sample at the multiple low frequencies less than 5000 Hz.

In embodiments, the multiple low frequencies less than 5000 Hz can comprise at least three frequencies less than or equal to 100 Hz (and possibly a set of at least three frequencies between 100 Hz and 1 Hz).

In embodiments, the parameter of the computational model as well as the parameter extracted from the measurement of permittivity of the porous media sample can be selected from the group consisting of a frequency-specific slope, a frequency-specific permittivity, a critical frequency where the measurement of permittivity of the porous media sample diverges from permittivity of porous media that does not have clay, and combinations thereof.

In embodiments, the at least one clay type can be selected from the group consisting of kaolinite, smectite, illite, chlorite, and combinations thereof.

In embodiments, the porous media sample can be a formation rock sample. In this case, the data that characterizes at least one clay type and corresponding clay volume fraction as output from the computational model can be used to calculate a value of cation exchange capacity (CEC) for the formation rock sample. The data that characterizes at least one clay type and corresponding clay volume fraction as output from the computational model can also be used for evaluation of a hydrocarbon reservoir corresponding to the formation rock sample.

In embodiments, the extracting of the parameter can be performed by a processor. The computational model can also be embodied by a processor. The operations of the method or system or parts thereof can also be controlled by a processor.

In embodiments, the surface location can be a laboratory, a wellsite or other surface location.

BRIEF DESCRIPTION OF THE DRAWINGS

The subject disclosure is further described in the detailed description which follows, in reference to the noted plurality of drawings by way of non-limiting examples of the subject disclosure, in which like reference numerals represent similar parts throughout the several views of the drawings, and wherein.

DETAILED DESCRIPTION

The particulars shown herein are by way of example and for purposes of illustrative discussion of the embodiments of the subject disclosure only and are presented in the cause of providing what is believed to be the most useful and readily understood description of the principles and conceptual aspects of the subject disclosure. In this regard, no attempt is made to show structural details in more detail than is necessary for the fundamental understanding of the subject disclosure, the description taken with the drawings making apparent to those skilled in the art how the several forms of the subject disclosure may be embodied in practice. Furthermore, like reference numbers and designations in the various drawings indicate like elements.

Interfacial polarization can be observed in formation rock containing clays (such as shaly sands) and in other porous media containing clays. When the surface of a nonconductive mineral, such as clay minerals and silica grains, are exposed to electrolytes, it acquires charges due to ionic adsorption, protonation/deprotonation of the hydroxyl groups, and dissociation of other potentially active surface groups. In the presence of an external electromagnetic (EM) field, these surface charges form electric dipoles and cause interfacial polarization (IP) effects. The strength of the IP effects is regulated by permittivity of the formation rock or other porous media.

The present disclosure provides a framework or methodology for clay detection, clay typing, and clay volume quantification using electromagnetic measurements on a formation rock sample that are scattered or dispersed at low frequencies (below 5000 Hz). The result of such low frequency electromagnetic measurements can be used to determine permittivity data that characterizes permittivity of the formation rock sample at the low frequencies (below 5000 Hz). The low frequency electromagnetic measurements can be performed in a laboratory, at a wellsite or other surface location. The low frequency electromagnetic measurements are nondestructive, and the results indicate that the methodology is with high sensitivity to the existence of clays compared to other conventional specialized mineralogical and elemental clay quantification methods such as x-ray diffraction, x-ray fluorescence, and Fourier-transform infrared spectroscopy.

The framework can also be used to evaluate porous media beyond reservoir rock evaluation in the oil and gas industry, such as quality screening for rock quarry sites, quality control of building stones and fracking sands, and quality assurance for optimized composition of cement in civil construction/well cementing and drilling fluids (considering sand is part of the mixture).

In embodiments, clay minerals can be lumped together on the basis of molecular structure and composition into four commonly encountered and representative clay types: kaolinite, illite, chlorite and smectite. Although each one of these clay types impacts formation conductivity differently, the fundamental mechanism is similar. When the surface of a clay mineral grain is exposed to electrolytes, it acquires charges due to ionic adsorption, protonation/deprotonation of the hydroxyl groups, and dissociation of other potentially active surface groups.

Under an external electromagnetic (EM) field, both electrical conduction (due to charge carries) and interfacial polarization (due to surface charges) influences the measured EM fields. Electrical conduction describes the movement of the charge carries under the influence of the external EM field. This is a well understood phenomena and can be described by Ohm's law.

Figure 1:
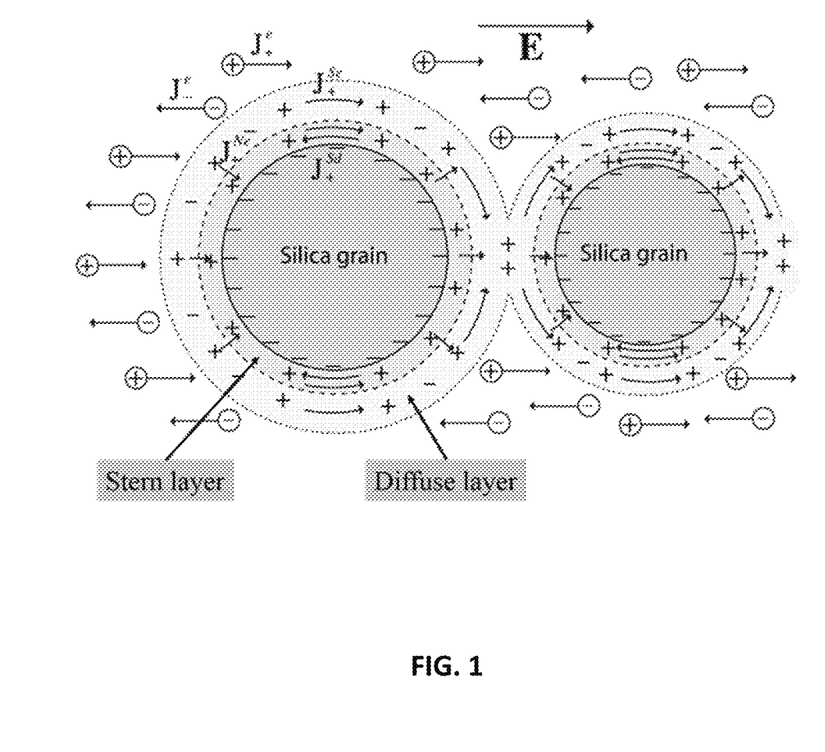
FIG. 1 is a schematic diagram illustrating an electrical double layer model of interfacial polarization of clay particles.

The polarization of clay particles is mostly due to charge accumulation and movements at host-inclusion interfaces. The most common theory to describe the interfacial polarization is the electrical double layer shown in FIG. 1. At the surface of the clay particles, both Stern and diffuse layers are formed due to charge absorptions and movements. In the presence of an applied external electromagnetic field, the double layer develops a counter ion cloud and diffused-charge distribution around host-inclusion interfaces. Dynamics of accumulation/depletion of charge concentrations around host-inclusion interfaces influence the magnitude and phase of the EM response of the formation rock containing clay minerals or other porous media containing clay minerals. The electrical conductivity of the porous media can be described by a complex conductivity $\sigma$ given by:

$$\sigma = \sigma^R + i\omega\varepsilon_0\varepsilon_r, \text{ and} \qquad \text{Eqn. (1a)}$$

$$\text{or } \sigma = \sigma^R + i\omega\varepsilon_{\mathit{eff}} \qquad \text{Eqn. (1b)}$$

where $\sigma^R$ is the in-phase component and $\omega\varepsilon_0\varepsilon_r$ is the quadrature (out-phase) component of a complex conductivity $\sigma$, respectively; $\omega$, is frequency, $\varepsilon_0$ is the permittivity of vacuum (e.g., 8.854×10$^{-12}$ F m$^1$), $\varepsilon_r$ is the relative permittivity, and $\varepsilon_{\mathit{eff}}$ is the effective permittivity given by the product $\varepsilon_0 \varepsilon_r$.

For a porous media containing clay minerals, the relative permittivity $\varepsilon_r$ and the effective permittivity $\varepsilon_{\mathit{eff}}$ depend on clay type and volume of each clay type. In addition, the relative permittivity $\varepsilon_r$ and the effective permittivity $\varepsilon_{\mathit{eff}}$ can be calculated based on effective media theory. In embodiments, the EM response signal of the porous media can be detected by one or more receiver antennae (e.g., receiver coil(s)). Phased-lock detection and amplification of the EM response signal can determine the amplitude and phase of the voltage levels detected by the one or more receiver antennae. By recording and processing the amplitude and phase of such voltage levels, a measurement of the complex conductivity σ of the porous media can be obtained. The relative permittivity $\varepsilon_r$ and/or the effective permittivity $\varepsilon_{eff}$ of the porous media can be extracted from the quadrature component of the complex conductivity σ according to eqns. (1a) and (1b) as set forth above.

Figure 2:
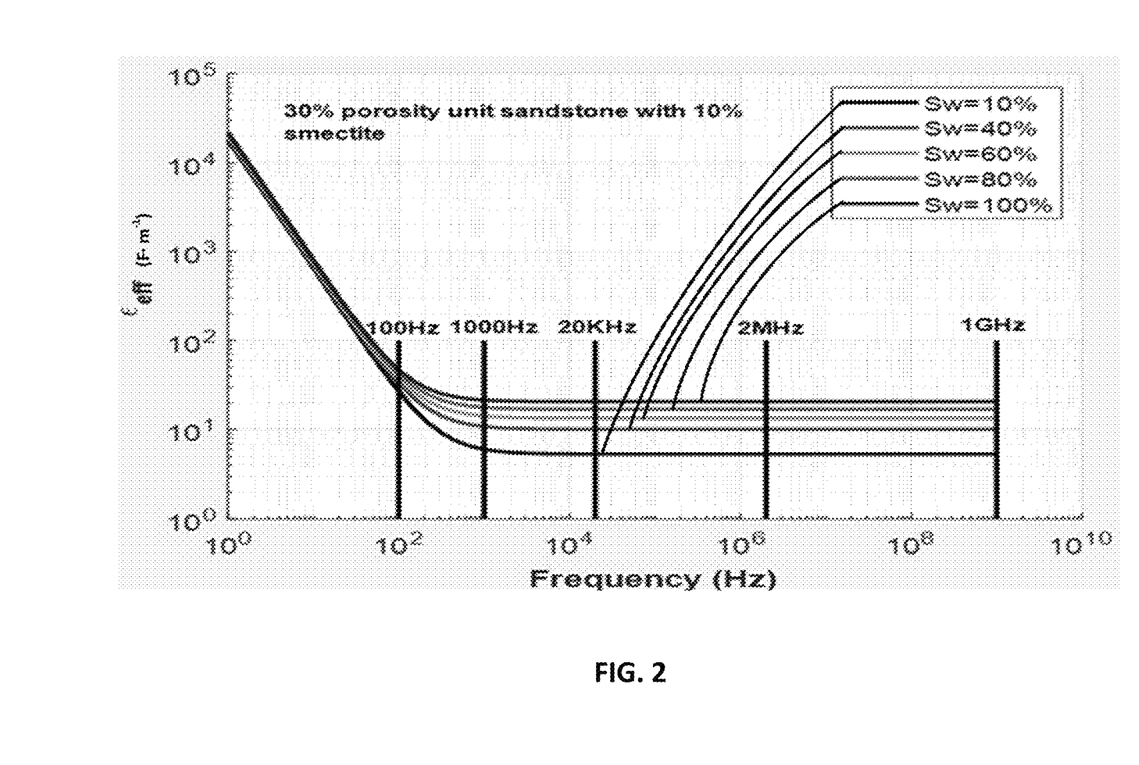
FIG. 2 depicts plots of relative permittivity $\varepsilon_r$ computed as a function of frequency (in Hz) for a shaly sandstone formation rock under different saturation conditions (including 10% water saturation/90% oil saturation, 40% water saturation/60% oil saturation, 60% water saturation/40% oil saturation, 80% water saturation/20% oil saturation, and 100% water saturation/0% oil saturation)

FIG. 2 shows relative permittivity $\varepsilon_r$ (no unit) computed as a function of frequency (in Hz) for a shaly sandstone formation rock under different saturation conditions (including 10% water saturation/90% oil saturation, 40% water saturation/60% oil saturation, 60% water saturation/40% oil saturation, 80% water saturation/20% oil saturation, and 100% water saturation). The shaly sandstone formation rock has 90% quartz and 10% smectite with a total porosity of 30%. Very strong dispersion effects are observed below 1000 Hz. The largest permittivity value can reach $2 \times 10^4$ at 1 Hz. For frequencies larger than 1000 Hz, the permittivity has much smaller values and is non-dispersive. Note that while parts of the curves show dependence on saturations, the dispersion section of the curves, for example in frequencies less than 100 Hz, is very insensitive to saturation. This implies that the measurement of relative permittivity $\varepsilon_r$ of formation rock as a function of frequency at low frequencies less than 100 Hz is a sensitive indicator for clay detection and quantification of clay volumes irrespective of the saturation conditions of the formation rock.

Figure 3:
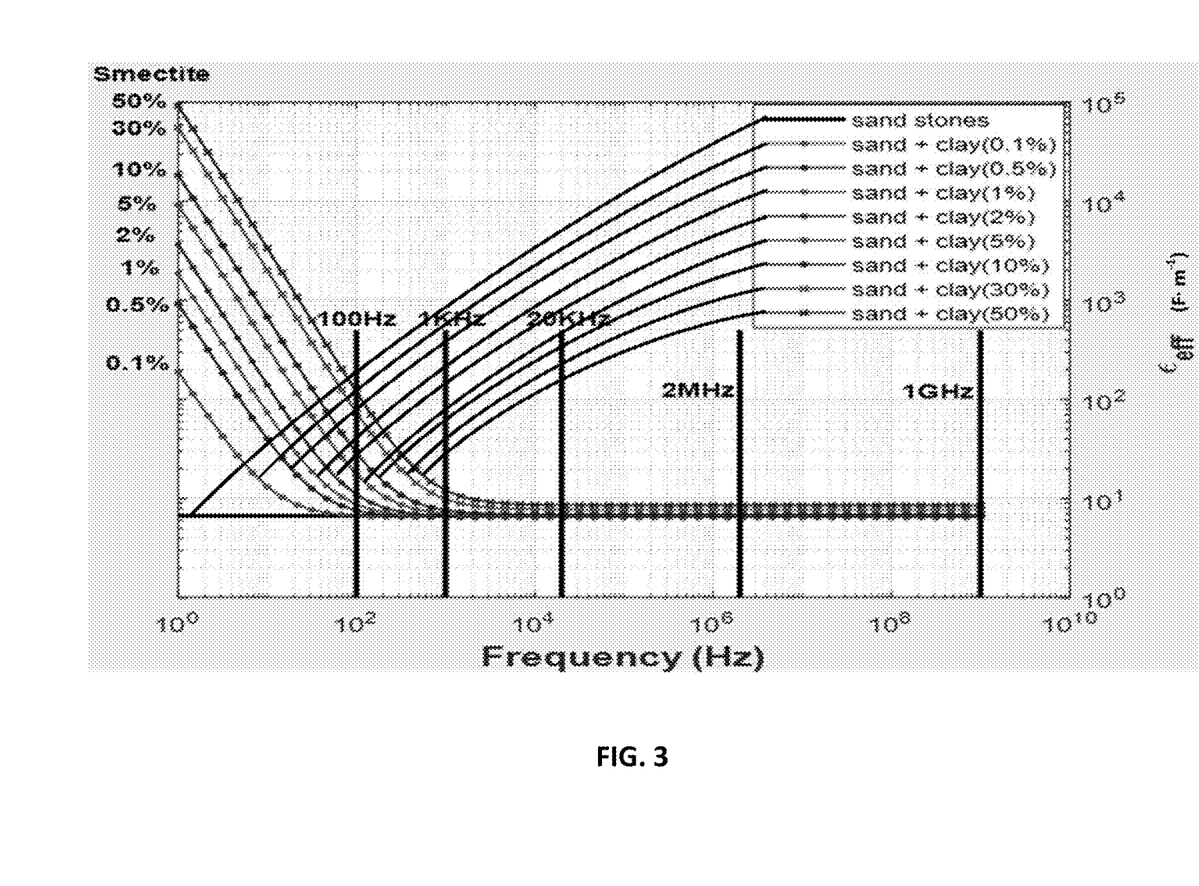
FIG. 3 depicts plots of relative permittivity $\varepsilon_r$ computed as a function of frequency (in Hz) for quartz mixed with smectite of different volume fractions (including 0.1%, 0.5%, 1%, 2%, 5%, 10%, 30% and 50%). For comparison, the relative permittivity $\varepsilon_r$ computed as a function of frequency for clean sandstone (pure quartz) is also plotted. All the curves have a water saturation level of 20% and an oil saturation level of 80%.

FIG. 3 shows relative permittivity $\varepsilon_r$ (no unit) computed as a function of frequency (in Hz) for quartz mixed with smectite of different volume fractions (including 0.1%, 0.5%, 1%, 2%, 5%, 10%, 30% and 50%). For comparison, the relative permittivity $\varepsilon_r$ (no unit) computed as a function of frequency (in Hz) for clean sandstone (pure quartz) is also plotted. All the curves have a water saturation level of 20% and an oil saturation level of 80%. It is observed that while the clean sandstone has no dispersion effect, the shaly sandstone shows strong dispersion effects. Specifically, the relative permittivities of the formation rock samples at a low frequency such as 1 Hz strongly depends on the respective volume fractions of the smectite clay component in the formation rock samples. Even with 1% or less clay content, the dispersion curves show a huge difference from the clean sandstone, indicating the measurement of relative permittivity of the formation rock sample at a low frequency (such as, for example, 1 Hz) is a very sensitive technique to detect small amount of clays for characterization of the clay components of the formation rock sample. In addition, the descending values of the relative permittivities of the formation rock samples at the low frequency (such as, for example, 1 Hz) are easily differentiable for different volume fractions of the smectite clay component in the formation rock samples. The sensitivity to differentiate clean and slightly shaly rock appears to be an improvement over downhole nuclear elemental spectroscopy measurements as described herein.

Figure 4:
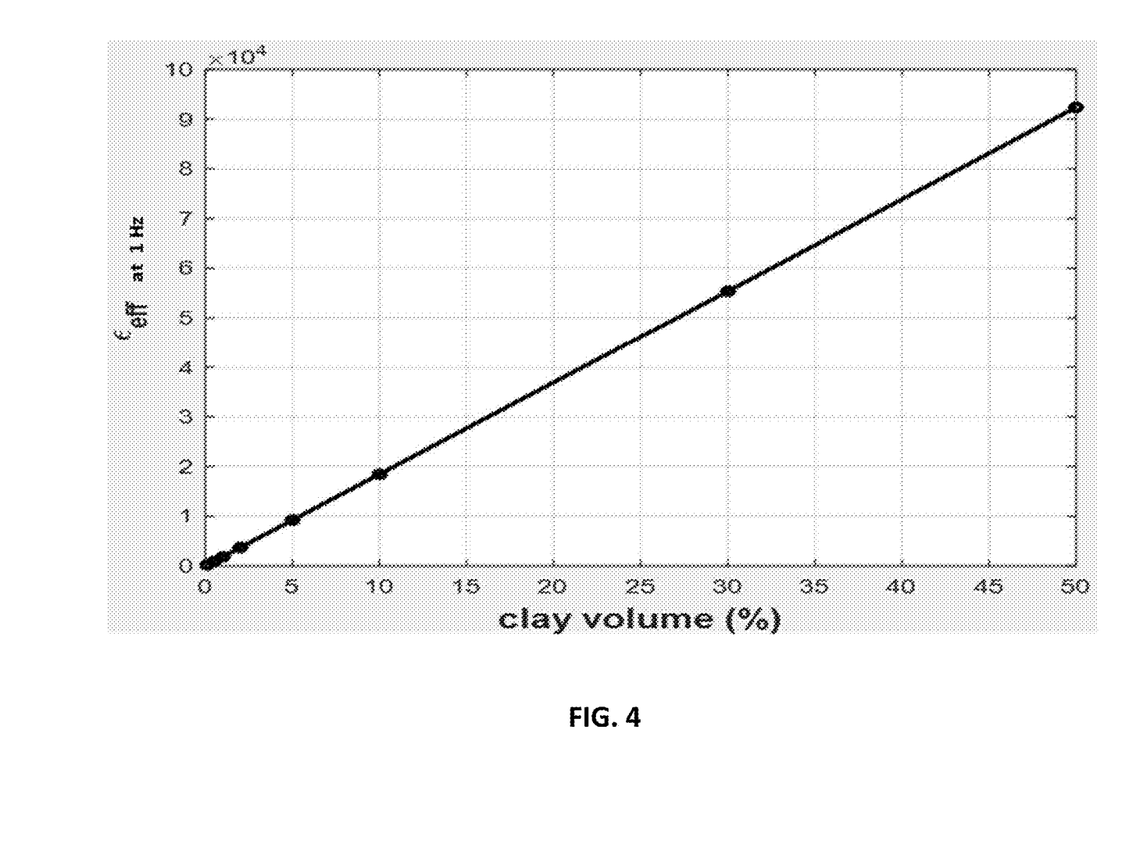
FIG. 4 depicts a correlation curve that represents a relationship between relative permittivity at 1 Hz ($\varepsilon_r$, 1 Hz) and a volume fraction of smectite clay ($V_{smectite}$) using data extracted from the measurements of FIG. 3.

In order to quantify clay volume, a computational model can be built that relates measurements of relative permittivity (or effective permittivity) at one or more low frequencies less than 5000 Hz to clay volume fraction. In embodiments, the computational model can relate measurements of relative permittivity (or effective permittivity) at multiple (at least three) low frequencies (e.g. 1 Hz, 10 Hz and 100 Hz) to clay volume fraction. For example, measurements of relative permittivity of a formation rock sample at 1 Hz can be related to clay volume fraction as shown in the correlation curve of FIG. 4, which shows a relationship between relative permittivity at 1 Hz ($\varepsilon_r$, 1 Hz) and a volume fraction of smectite clay ($v_{smectite}$) using data extracted from the measurements of FIG. 3. This relationship demonstrates the sensitivity of low frequency permittivity on smectite clay volume and can be represented by:

$$\varepsilon_r, 1\,Hz = 1856.7 * V_{smectite} + 7.0, \text{ or} \qquad \text{Eqn. (2a)}$$

$$\text{or } v_{smectite} = \frac{\varepsilon_{r,1\,Hz} - \varepsilon_{r,clean\,rock}}{\text{Slope}} = \frac{\varepsilon_{r,1\,Hz} - 7.0}{1856.7} \qquad \text{Eqn. (2b)}$$

Note that the relationship of FIG. 4 and Eqns. (2a) and (2b) is an example, and thus other correlations and computational models can be used depending on the clay type, clay volume and a mixture of different clay types and clay volumes. Laboratory measurements of relative permittivity (or effective permittivity) at the low frequency(ies) on reservoir rock samples of known or measured clay volumes can be used to determine the relationship between measured permittivity at one or more low frequencies and clay volume fractions individually or in mixtures.

Figure 5:
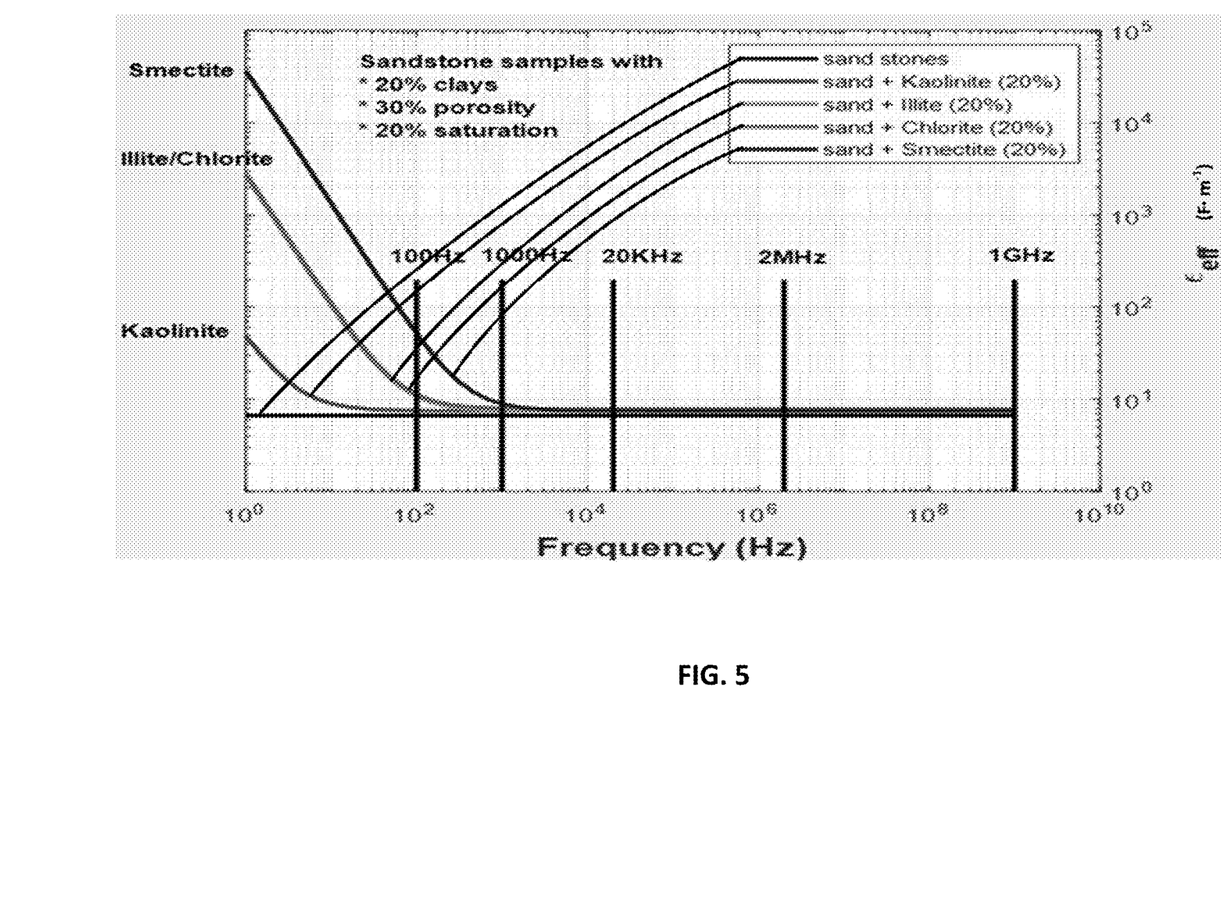
FIG. 5 depicts a plot of relative permittivity $\varepsilon_r$ computed as a function of frequency (in Hz) for sandstone samples mixed with different clay types (kaolinite, illite, chlorite and smectite) of the same 20% volume fraction with a total porosity of 30%. For comparison, the relative permittivity $\varepsilon_r$ computed as a function of frequency for a clean sandstone sample (no clay) is also plotted. All the curves have a water saturation level of 20% and an oil saturation level of 80%.

FIG. 5 shows relative permittivity $\varepsilon_r$ (no unit) computed as a function of frequency (in Hz) for sandstone samples mixed with different clay types (kaolinite, illite, chlorite and smectite) of the same 20% volume fraction with a total porosity of 30%. For comparison, the relative permittivity $\varepsilon_r$ (no unit) computed as a function of frequency (in Hz) for a clean sandstone sample (no clay) is also plotted. All the curves have a water saturation level of 20% and an oil saturation level of 80%. It is clearly observed that smectite and kaolinite have different relative permittivities at a low frequency such as 1 Hz, which are easily distinguishable from one another. More specifically, the sandstone sample mixed with kaolinite at 20% volume fraction has a relative permittivity on the order of 40, while the sandstone sample mixed with smectite at 20% volume fraction has a relative permittivity $\varepsilon_r$ on the order of 2.5. Furthermore, it is clearly observed that smectite and kaolinite have different critical frequencies where the measured effective permittivity deviates significantly from that of clean sandstone. More specifically, the sandstone sample mixed with kaolinite at 20% volume fraction has a critical frequency at or near 10 Hz, while the sandstone sample mixed with smectite at 20% volume fraction has a critical frequency near 900 Hz. Note that these two parameters of the measured permittivity at a low frequency cannot be used to distinguish the illite and chlorite clay types because these two clay types have almost the same electric properties. In practical applications, permittivities at multiple low frequencies (e.g. 1 Hz, 10 Hz and 100 Hz) can be measured on core samples of the known different clay types (including the kaolinite, illite, chlorite, smectite and combinations of such clay types) and of known different clay type volume fractions, and such measurements can be processed in order to build a computational model (such as a correlation model) that relates parameters extracted from low frequency permittivity measurements into one or more clay types and corresponding clay type volume fractions.

The following conclusions can be based on FIGS. 2, 3, 4 and 5.

First, measurements of relative permittivity $\varepsilon_r$ (or effective permittivity $\varepsilon_{eff}$) as a function of frequency at low frequencies have almost no dependence on water saturation of shaly sandstone formation rock. This makes such measurements an ideal clay detector for all saturation conditions, pay zones or otherwise.

Second, the measurements of relative permittivity $\varepsilon_r$ (or effective permittivity $\varepsilon_{eff}$) of the formation rock at low frequencies (such as less than 1000 Hz) strongly depends on clay volume fractions for shaly sandstone formation rock. Even with 1% or less clay content, the effective permittivity $\varepsilon_{eff}$ (or relative permittivity $\varepsilon_r$) of the formation rock at the low frequency shows a huge difference from that of clean sandstone. In addition, for formation rocks with different clay volume fractions, the relative permittivities (or effective permittivities) of the formation rocks at low frequency are easily differentiable for the different clay volume fractions.

Third, the measurements of relative permittivity $\varepsilon_r$ (or effective permittivity $\varepsilon_{eff}$) of formation rock at low frequencies (such as less than 1000 Hz) also strongly depends on clay types for shaly sandstone formation rock. Furthermore, the presence of smectite and kaolinite clay types that commonly occur in a reservoir environment can be detected based on the measurements of relative permittivity $\varepsilon_r$ (or effective permittivity $\varepsilon_{eff}$) of formation rock at low frequency (such as less than 1000 Hz). For example, the measurement of relative permittivity $\varepsilon_r$ (or effective permittivity $\varepsilon_{eff}$) of formation rock at a low frequency such as 1 Hz and/or the critical frequency that relative permittivity $\varepsilon_r$ (or effective permittivity $\varepsilon_{eff}$) of formation rock deviates from that of clean sandstone can be used to detect the presence of smectite and kaolinite clay types. Note that these measurements cannot distinguish between illite and chlorite clay types as these two clays have almost the same electric properties.

Fourth, in order to detect different clays types (including smectite, kaolinite, illite and chlorite and combinations thereof) and to quantify the corresponding volume fraction of the different clay types, the relative permittivity $\varepsilon_r$ (or the effective permittivity $\varepsilon_{eff}$) of the formation rock can be measured at multiple low frequencies below 5000 Hz. One or more parameters (such as a frequency-specific slope or frequency-specific measure(s) of permittivity) can be extracted from the multiple low frequency permittivity measurements and used in conjunction with a computational model (such as a correlation model) that relates such parameters to one or more clay types (such as smectite, kaolinite, illite, chlorite, and combinations thereof) and corresponding clay type volume fractions.

Figure 6:
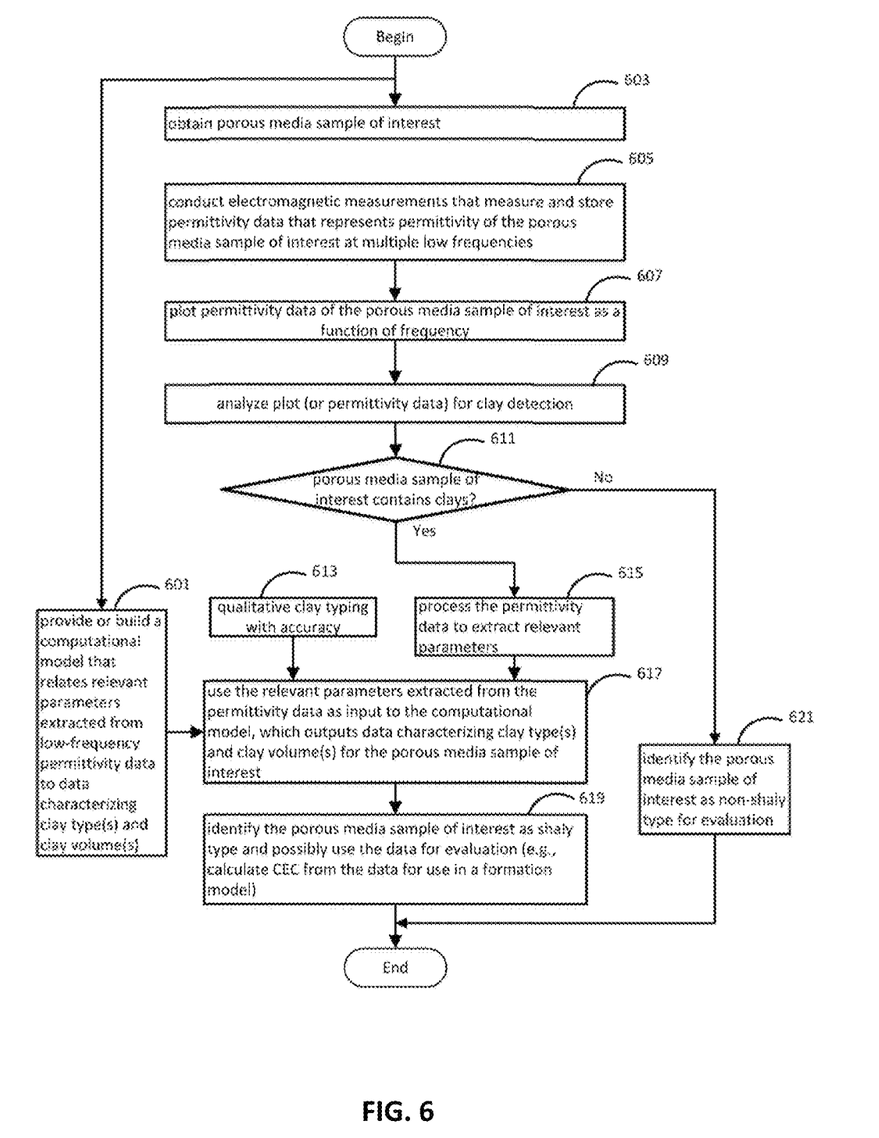
FIG. 6 is a flowchart illustrating a methodology for clay detection, clay typing, and clay volume quantification using electromagnetic measurements on a porous media sample that are dispersed at low frequencies (below 5000 Hz). The low frequency electromagnetic measurements are used to determine permittivity data that characterizes permittivity of the porous media sample at the low frequencies (below 5000 Hz)

FIG. 6 depicts a workflow for clay detection, clay typing, and clay volume quantification using electromagnetic measurements of the permittivity of a porous media sample of interest that are scattered or dispersed at low frequencies (below 5000 Hz).

In block 601, a computational model is built (or provided) that relates relevant parameters extracted from low frequency permittivity data (which is data derived from low frequency electromagnetic measurements that are used to determine permittivity of a porous media sample) to data characterizing clay type(s) and clay volume fraction(s) of the porous media sample. The computational model can be built by conducting electromagnetic measurements and determinations of permittivity of porous media samples of known different clay types (including kaolinite, illite, chlorite, smectite and combinations of such clay types) and of known different clay type volume fractions at multiple low frequencies (e.g. 1 Hz, 10 Hz and 100 Hz). Such low frequency electromagnetic measurements can be used to determine permittivity data that characterizes the permittivity of the porous media samples at the multiple low frequencies. The permittivity data can represent effective permittivity or relative permittivity of porous media samples. Such low frequency electromagnetic measurements can involve applying a time varying external electromagnetic field to each porous media sample and measuring the magnitude and phase of the electromagnetic response of the porous media sample. For each one of the multiple low frequencies (e.g. 1 Hz, 10 Hz and 100 Hz) of the experiment, the frequency of the applied time varying external electromagnetic field is controlled to correspond to the particular low frequency and the electromagnetic response of the porous media sample is measured at that particular low frequency. Permittivity data can be determined by processing the measured electromagnetic response of the porous media sample at that particular low frequency. The permittivity data that results from such low frequency electromagnetic measurements can be processed to extract one or more relevant parameters from the low frequency permittivity data (such as a frequency-specific slope or frequency-specific measure(s) of permittivity or critical frequency) and determine a correlation function or other data structure that describes the relationship between the extracted relevant parameter(s) and one or more clay types and corresponding clay type volume fractions. The correlation function or other data structure can then be integrated as part of the computational model. The computational model can be designed to take as input one or more relevant parameters extracted from low frequency permittivity data. The correlation function or other data structure of the computational model is used to output one or more clay types and corresponding clay type volume fractions that correspond to the relevant parameter(s) supplied as input to the computational model. The low frequency electromagnetic measurements of the permittivity of the porous media sample that are used to build the computational model can be performed in a laboratory or other surface location. In oilfield applications, the porous media samples used to build the computational model in block 601 can be rock core samples that are saturated with formation fluids or other rock samples. In other applications, other porous media samples (such as, but not limited to, outcrops, building blocks, cement, other porous building materials, etc.) can be used to build the computational model in block 601.

In block 603, a porous media sample of interest is obtained. In oilfield applications, the porous media sample of interest can be a rock core sample that is saturated with formation fluids or some other rock sample. The rock sample can be extracted or otherwise obtained from a hydrocarbon reservoir. In other applications, other porous media samples (such as, but not limited to, outcrops, building blocks, cement, other porous building materials, etc.) can be used.

In block 605, electromagnetic measurements are conducted on the porous media sample of interest obtained in 603 at multiple low frequencies (e.g. 1 Hz, 10 Hz and 100 Hz). Such low frequency electromagnetic measurements can be used to determine permittivity data that characterizes the permittivity of the porous media sample of interest at the multiple low frequencies. The permittivity data can represent relative permittivity or effective permittivity of the porous media sample of interest. Such electromagnetic measurements can involve applying a time varying external electromagnetic field to the porous media sample of interest and detecting the magnitude and phase of the electromagnetic response of the porous media sample of interest to derive a measurement of the complex conductivity of the porous media sample of interest. Relative permittivity and/or effective permittivity of the porous media sample of interest can be extracted from the quadrature component of the complex conductivity according to Eqn. (1a) and (1b) as set forth above. For each one of the multiple low frequencies (e.g. 1 Hz, 10 Hz and 100 Hz) of the experiment, the frequency of the applied time varying external electromagnetic field is controlled to correspond to the particular low frequency and the electromagnetic response of the porous media sample of interest is measured at that particular low frequency. The low frequency electromagnetic measurements of the porous media sample of interest can be performed in a laboratory, at a wellsite or other surface location.

In blocks 607, 609, and 611, the permittivity data measured and stored in block 605, which represents permittivities of the porous media sample of interest as a function of frequency, can be analyzed for clay detection and qualitative clay assessment. For example, the permittivity data measured and stored in block 605 can be plotted in block 607 and the plot (or the permittivity data itself) can be analyzed for clay detection in block 609. For example, the plot (or the permittivity data itself) can be compared to measured permittivity values (e.g. curves) for one or more porous media samples (e.g., rock samples) that are known to not have clay as well as to measured permittivity values (e.g. curves) for one or more porous media samples (e.g. rock samples) of known clay types. If the permittivity data measured and stored in block 605 is dissimilar to the measured permittivity values (e.g. curves) for the one or more porous media samples (e.g., rock samples) that are known to not have clay and similar to the measured permittivity values (e.g. curves) for one or more porous media samples (e.g., rock samples) of known clay types, the process can determine that the porous media sample of interest does contain clays in block 611 and continue to blocks 615 to 619. On the other hand, when the permittivity data measured and stored in block 605 is similar to measured permittivity values (e.g. curves) for the one or more porous media samples (e.g., rock samples) that are known to not have clay and dissimilar to the measured permittivity values (e.g. curves) for the one or more porous media samples (e.g., rock samples) of known clay types, the process can determine in block 611 that the porous media sample of interest does not contain clays and continue to block 621.

In block 613, the porous media sample of interest (or other related sample(s)) can be evaluated for qualitative clay assessment with accuracy. For example, the permittivity data measured and stored in block 605 can be plotted and compared to measured permittivity values (e.g. curves) for one or more porous media samples (e.g., rock samples) of known clay types. The known clay type of the porous media sample (e.g., rock sample) whose measured permittivity values best match the permittivity data measured and stored in block 605 for the porous media sample of interest can be identified as the clay type for the porous media sample of interest. Additionally or alternatively, the porous media sample of interest (or other related sample(s)) can be subject to physical examination (such as, but not limited to SEM measurements and thin section measurements) in order to identify the clay type for the porous sample of interest. Such physical measurements can be selected and configured in order to properly identify the clay type for the porous sample of interest with high precision especially at low level of clay content.

In block 615, the permittivity data measured and stored in block 605 can be processed to extract relevant parameter(s) of such data for input to the computational model of block 601.

In block 617, the relevant parameter(s) extracted in block 615 can be used as input to the computational model, which outputs data characterizing one or more clay types and corresponding clay volume fractions for the porous media sample of interest. The data characterizing one or more clay types and corresponding clay volume fractions for the porous media sample of interest as output by the computational model can be stored in computer memory for subsequent access or possibly output for analysis.

In block 619, the process can identify the porous media sample of interest as shaly type and possibly use the data that characterizes the one or more clay types and corresponding clay volume fractions as output from the computational model in block 617 to evaluate the porous media sample of interest or related porous media. For example, in oilfield applications where the porous media sample of interest is a rock sample, the data that characterizes the one or more clay types and corresponding clay volume fractions as output from the computational model in block 617 can be used to evaluate the hydrocarbon reservoir from which the rock sample was obtained.

In embodiments, the data that characterizes the one or more clay types and corresponding clay volume fractions as output from the computational model in block 617 can be used to calculate a value of cation exchange capacity (CEC) for the formation rock. The value of CEC represents a quantity of positively charged ions (cations) that the formation rock can accommodate on its negative charged surface. It is typically expressed as milliequivalents per 100 grams. The CEC value can be used in formation modeling and simulation of the hydrocarbon reservoir from which the formation rock sample of interest was obtained.

For example, if both clay types and clay volume fractions are known for each clay type, the total CEC values can be calculated using a mixing law as follows:

$$CEC = w_C \times CEC_C + w_I \times CEC_I + w_K \times CEC_K + w_S \times CEC_S, \qquad \text{Eqn. (3)}$$

where $w_C$, $w_I$, $w_K$, $w_S$ are clay weight fractions for chlorite, illite, kaolinite and smectite, respectively; and $CEC_C$, $CEC_I$, $CEC_K$ and $CEC_S$ are CEC values for chlorite, illite, kaolinite and smectite.

The CEC value for each above-mentioned clay mineral is well defined and can be treated as a known parameter. For example, the clay volume can be calculated as follows:

$$V_{cl} = \frac{\rho_{matrix}(1 - \phi_{total}) \times W_{cl}}{\rho_{cl}}, \qquad \text{Eqn. (4)}$$

where $\phi_{total}$ is the formation total porosity, $\rho_{matrix}$ is matrix density, $W_{cl}$ is weight of clay, and $\rho_{cl}$ is density of clay.

In block 621, the process can identify the porous media sample of interest as non-shaly type for evaluation of the porous media sample of interest or related porous media.

Note that in some applications, it is common for the porous media sample to be saturated with a mixture of water (e.g., brine) and oil, a mixture of water (e.g., brine) and hydrocarbon gas, or possibly a mixture of water (e.g., brine), oil and hydrocarbon gas. In order to address these different scenarios, the computational model can be configured to relate permittivity of the porous media sample to the minerology data (clay type and clay volume fractions) for one or more of these different scenarios.

Moreover, the porous media samples that are tested can be small (such as in the lab samples) or large (such as in on-site samples).

Furthermore, the clay types can be the four clay types commonly encountered in subsurface formations, or other special type of clays such as sepiolite.

Figure 7:
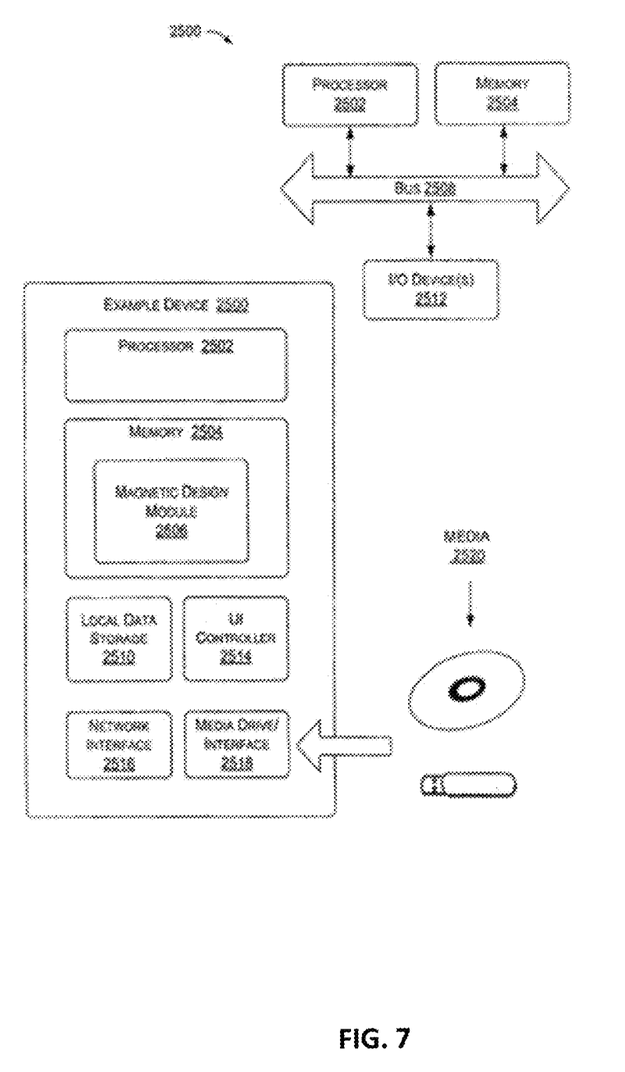
FIG. 7 is a block diagram of a computer processing system, which can be used to embody parts of the methodology for clay detection, clay typing, and clay volume quantification as described herein.

FIG. 7 illustrates an example device 2500, with a processor 2502 and memory 2504 that can be configured to implement various embodiments of the framework as discussed in this disclosure. Memory 2504 can also host one or more databases and can include one or more forms of volatile data storage media such as random-access memory (RAM), and/or one or more forms of nonvolatile storage media (such as read-only memory (ROM), flash memory, and so forth).

Device 2500 is one example of a computing device or programmable device and is not intended to suggest any limitation as to scope of use or functionality of device 2500 and/or its possible architectures. For example, device 2500 can comprise one or more computing devices, programmable logic controllers (PLCs), etc.

Further, device 2500 should not be interpreted as having any dependency relating to one or a combination of components illustrated in device 2500. For example, device 2500 may include one or more of computers, such as a laptop computer, a desktop computer, a mainframe computer, etc., or any combination or accumulation thereof.

Device 2500 can also include a bus 2508 configured to allow various components and devices, such as processors 2502, memory 2504, and local data storage 2510, among other components, to communicate with each other.

Bus 2508 can include one or more of any of several types of bus structures, including a memory bus or memory controller, a peripheral bus, an accelerated graphics port, and a processor or local bus using any of a variety of bus architectures. Bus 2508 can also include wired and/or wireless buses.

Local data storage 2510 can include fixed media (e.g., RAM, ROM, a fixed hard drive, etc.) as well as removable media (e.g., a flash memory drive, a removable hard drive, optical disks, magnetic disks, and so forth).

One or more input/output (I/O) device(s) 2512 may also communicate via a user interface (UI) controller 2514, which may connect with I/O device(s) 2512 either directly or through bus 2508.

In one possible implementation, a network interface 2516 may communicate outside of device 2500 via a connected network.

A media drive/interface 2518 can accept removable tangible media 2520, such as flash drives, optical disks, removable hard drives, software products, etc. In one possible implementation, logic, computing instructions, and/or software programs comprising elements of module 2506 may reside on removable media 2520 readable by media drive/interface 2518.

In one possible embodiment, input/output device(s) 2512 can allow a user (such as a human annotator) to enter commands and information to device 2500, and also allow information to be presented to the user and/or other components or devices. Examples of input device(s) 2512 include, for example, sensors, a keyboard, a cursor control device (e.g., a mouse), a microphone, a scanner, and any other input devices known in the art. Examples of output devices include a display device (e.g., a monitor or projector), speakers, a printer, a network card, and so on.

Some of the methods and processes described above, can be performed by a processor. The term "processor" should not be construed to limit the embodiments disclosed herein to any particular device type or system. The processor may include a computer system. The computer system may also include a computer processor (e.g., a microprocessor, microcontroller, digital signal processor, or general-purpose computer) for executing any of the methods and processes described above.

The computer system may further include a memory such as a semiconductor memory device (e.g., a RAM, ROM, PROM, EEPROM, or Flash-Programmable RAM), a magnetic memory device (e.g., a diskette or fixed disk), an optical memory device (e.g., a CD-ROM), a PC card (e.g., PCMCIA card), or other memory device.

Some of the methods and processes described above, can be implemented as computer program logic for use with the computer processor. The computer program logic may be embodied in various forms, including a source code form or a computer executable form. Source code may include a series of computer program instructions in a variety of programming languages (e.g., an object code, an assembly language, or a high-level language such as C, C++, or JAVA). Such computer instructions can be stored in a non-transitory computer readable medium (e.g., memory) and executed by the computer processor. The computer instructions may be distributed in any form as a removable storage medium with accompanying printed or electronic documentation (e.g., shrink wrapped software), preloaded with a computer system (e.g., on system ROM or fixed disk), or distributed from a server or electronic bulletin board over a communication system (e.g., the Internet or World Wide Web).

Alternatively or additionally, the processor may include discrete electronic components coupled to a printed circuit board, integrated circuitry (e.g., Application Specific Integrated Circuits (ASIC)), and/or programmable logic devices (e.g., a Field Programmable Gate Arrays (FPGA)). Any of the methods and processes described above can be implemented using such logic devices.

Although only a few examples have been described in detail above, those skilled in the art will readily appreciate that many modifications are possible in the examples without materially departing from this subject disclosure. Accordingly, all such modifications are intended to be included within the scope of this disclosure as defined in the following claims. In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures. It is the express intention of the applicant not to invoke 35 U.S.C. § 112, paragraph 6 for any limitations of any of the claims herein, except for those in which the claim expressly uses the words 'means for' together with an associated function.

What is claimed is:

1. A method for characterizing clay content of a porous media sample, the method comprising:
   i) conducting an electromagnetic measurement on the porous media sample at a low frequency less than 5000 Hz, wherein the electromagnetic measurement is used to determine and store permittivity data that characterizes permittivity of the porous media sample at the low frequency less than 5000 Hz;
   ii) extracting a parameter from the permittivity data that characterizes permittivity of the porous media sample at the low frequency less than 5000 Hz; and iii) using the parameter extracted from the permittivity data in ii) as input to a computational model, wherein the computational model relates the parameter extracted from the permittivity data in ii) to data that characterizes at least one clay type and corresponding clay volume fraction for the porous media sample, wherein the operations of i), ii), and iii) are performed at a surface location.

2. The method according to claim 1, further comprising:
storing or outputting the data that characterizes at least one clay type and corresponding clay volume fraction for the porous media sample as provided by the computational model in iii).

3. The method according to claim 1, wherein:
the computational model of iii) is derived by measuring permittivity of porous media of different known clay types and different clay volume fractions at the low frequency less than 5000 Hz and correlating a parameter extracted from the resultant permittivity to data that characterizes at least one clay type and corresponding clay volume fraction.

4. The method according to claim 1, wherein:
the computational model of iii) is derived by measuring permittivity of porous media of different known clay types and different clay volume fractions at multiple low frequencies less than 5000 Hz and correlating a parameter extracted from the resultant permittivity to data that characterizes at least one clay type and corresponding clay volume fraction.

5. The method according to claim 1, wherein:
the computational model of iii) relates a parameter extracted from measurement of permittivity of porous media at multiple low frequencies less than 5000 Hz to data that characterizes at least one clay type and corresponding clay volume fraction; and
the permittivity data of i) as well as the parameter extracted from the permittivity data in ii) are derived from electromagnetic measurements on the porous media sample at the multiple low frequencies less than 5000 Hz.

6. The method according to claim 5, wherein:
the multiple low frequencies less than 5000 Hz comprises at least three frequencies less than or equal to 100 Hz.

7. The method according to claim 5, wherein:
the multiple low frequencies less than 5000 Hz comprises a set of at least three frequencies between 100 Hz and 1 Hz.

8. The method according to claim 1, wherein:
the parameter extracted from the permittivity data in ii) and input to the computational model of iii) is selected from the group consisting of: a frequency-specific slope, a frequency-specific permittivity, a critical frequency where the measurement of permittivity of the porous media sample diverges from permittivity of porous media that does not have clay, and combinations thereof.

9. The method according to claim 1, wherein:
the permittivity data of i) represents relative permittivity or effective permittivity of the porous media sample.

10. The method according to claim 1, wherein:
the permittivity data of i) is derived from a quadrature component of a measurement of complex conductivity of the porous media sample.

11. The method according to claim 1, wherein:
the at least one clay type is selected from the group consisting of: kaolinite, smectite, illite, chlorite, and combinations thereof.

12. The method according to claim 1, wherein:
the porous media sample comprises a formation rock sample.

13. The method according to claim 12, further comprising:
using the data that characterizes at least one clay type and corresponding clay volume fraction as output from the computational model in iii) to calculate a value of cation exchange capacity (CEC) for the formation rock sample.

14. The method according to claim 12, further comprising:
using the data that characterizes at least one clay type and corresponding clay volume fraction as output from the computational model in iii) for evaluation of a hydrocarbon reservoir corresponding to the formation rock sample.

15. The method according to claim 1, wherein:
the extracting of the parameter in ii) is performed by a processor, or the computational model of iii) is embodied by a processor.

16. The method according to claim 1, wherein:
the surface location is selected from the group consisting of: a laboratory, a wellsite or other surface location.

17. The method according to claim 1, wherein conducting the electromagnetic measurement on the porous media sample comprises:
detecting an electromagnetic response signal with one or more receiver antennas, wherein phase-lock detection and amplification of the response signal is used to determine an amplitude and a phase of one or more voltage levels detected by the one or more receiver antennas; and
recording and processing the amplitude and phase of the one or more voltage levels to obtain a measurement of a complex conductivity (a) of the porous media, wherein the permittivity data in i) comprises the complex conductivity (a), and wherein the parameter extracted from the permittivity data that characterizes the permittivity of the porous media sample in ii) is extracted from a quadrature component of the complex conductivity.

18. A system for characterizing clay content of a porous media sample, the system comprising:
at least one receiver antenna that, when performing at least one electromagnetic measurement at a low frequency less than 5000 Hz on the porous media sample, is configured to detect at least one electromagnetic response signal of the porous media sample; and
at least one processor that, when executing program instructions stored in memory, is configured to:
i) build or provide a computational model that relates a parameter extracted from measurement of permittivity of porous media at the low frequency less than 5000 Hz to data that characterizes at least one clay type and corresponding clay volume fraction;
ii) obtain permittivity data that characterizes permittivity of the porous media sample at the low frequency less than 5000 Hz, wherein the permittivity data is derived from the at least one electromagnetic response signal of the porous media;
iii) extract a parameter from the permittivity data that characterizes permittivity of the porous media sample at the low frequency less than 5000 Hz; and
iv) use the parameter extracted from the permittivity data in iii) as input to the computational model of i), wherein the computational model outputs data that characterizes at least one clay type and corresponding clay volume fraction for the porous media sample, wherein the system is located at a surface location.

19. The system according to claim 18, wherein:

the at least one processor is further configured to store or output the data that characterizes at least one clay type and corresponding clay volume fraction for the porous media sample as provided by the computational model in iv).

20. The system according to claim 18, wherein:

the computational model of i) is derived by measuring permittivity of porous media of different known clay types and different clay volume fractions at the low frequency less than 5000 Hz and correlating a parameter extracted from the resultant permittivity to data that characterizes at least one clay type and corresponding clay volume fraction.

21. The system according to claim 18, wherein:

the computational model of i) is derived by measuring permittivity of porous media of different known clay types and different clay volume fractions at multiple low frequencies less than 5000 Hz and correlating a parameter extracted from the resultant permittivity to data that characterizes at least one clay type and corresponding clay volume fraction.

22. The system according to claim 18, wherein:

the computational model of i) relates a parameter extracted from measurement of permittivity of porous media at multiple low frequencies less than 5000 Hz to data that characterizes at least one clay type and corresponding clay volume fraction; and the permittivity data obtained in ii) as well as the parameter extracted from the permittivity data in iii) are derived from electromagnetic measurements performed on the porous media sample at the multiple low frequencies less than 5000 Hz.

23. The system according to claim 22, wherein:

the multiple low frequencies less than 5000 Hz comprises at least three frequencies less than or equal to 100 Hz.

24. The system according to claim 22, wherein:

the multiple low frequencies less than 5000 Hz comprises a set of at least three frequencies between 100 Hz and 1 Hz.

* * * * *